United States Patent
Zhong et al.

(10) Patent No.: US 9,055,898 B2
(45) Date of Patent: Jun. 16, 2015

(54) LANCET RELEASE MECHANISM

(75) Inventors: Weiping Zhong, Granger, IN (US);
Ernest Wise, Middlebury, IN (US)

(73) Assignee: Bayer HealthCare LLC, Whippany, NJ (US)

( * ) Notice: Subject to any disclaimer, the term of this patent is extended or adjusted under 35 U.S.C. 154(b) by 1483 days.

(21) Appl. No.: 11/885,521

(22) PCT Filed: Mar. 3, 2006

(86) PCT No.: PCT/US2006/007899
§ 371 (c)(1),
(2), (4) Date: Aug. 31, 2007

(87) PCT Pub. No.: WO2006/096630
PCT Pub. Date: Sep. 14, 2006

(65) Prior Publication Data
US 2008/0195133 A1 Aug. 14, 2008

Related U.S. Application Data

(60) Provisional application No. 60/658,650, filed on Mar. 4, 2005.

(51) Int. Cl.
*A61B 17/14* (2006.01)
*A61B 5/15* (2006.01)

(52) U.S. Cl.
CPC .................................. *A61B 5/1411* (2013.01)

(58) Field of Classification Search
CPC .................................................. A61B 5/1411
USPC ................................... 606/181, 182; 600/583
See application file for complete search history.

(56) References Cited

U.S. PATENT DOCUMENTS

| 3,797,488 A | 3/1974 | Hurschman et al. |
| 4,203,446 A | 5/1980 | Hofert et al. |

(Continued)

FOREIGN PATENT DOCUMENTS

| DE | 459 483 | 5/1928 |
| EP | 0 115 388 A1 | 8/1984 |

(Continued)

OTHER PUBLICATIONS

Written Opinion of the International Searching Authority corresponding to co-pending International Patent Application No. PCT/US2006/007899, European Patent Office, dated Jul. 31, 2006, 5 pages.

(Continued)

*Primary Examiner* — Kathleen Holwerda
*Assistant Examiner* — Sarah Simpson
(74) *Attorney, Agent, or Firm* — Nixon Peabody LLP

(57) ABSTRACT

A lancing device comprises a lancet holder and a lancet-release mechanism. The lancet holder forms an aperture. The aperture is adapted to receive a lancet assembly therein. The lancet holder is adapted to move the lancet assembly between a resting position, a cocking position, and a puncture position. The lancet-release mechanism includes a release button located adjacent to and external from the lancing device and a beam attached to the release button. The beam extends into the lancing device and the lancet holder. The beam is adapted to engage the lancet assembly. The release button and attached beam are adapted to eject the lancet assembly from the lancet holder.

19 Claims, 7 Drawing Sheets

(56) References Cited

U.S. PATENT DOCUMENTS

| | | | |
|---|---|---|---|
| 4,442,836 A * | 4/1984 | Meinecke et al. | 606/182 |
| 4,449,529 A | 5/1984 | Burns et al. | |
| 4,469,110 A | 9/1984 | Slama et al. | |
| 4,517,978 A | 5/1985 | Levin et al. | |
| 4,553,541 A | 11/1985 | Burns | |
| 4,627,445 A | 12/1986 | Garcia et al. | |
| 4,637,403 A | 1/1987 | Garcia et al. | |
| 4,735,203 A | 4/1988 | Ryder et al. | |
| D297,459 S | 8/1988 | Heiland et al. | |
| 4,787,398 A | 11/1988 | Garcia et al. | |
| RE32,922 E | 5/1989 | Levin et al. | |
| 4,924,879 A | 5/1990 | O'Brien | |
| 4,976,724 A | 12/1990 | Nieto et al. | |
| 4,990,154 A | 2/1991 | Brown et al. | |
| 5,074,872 A | 12/1991 | Brown et al. | |
| D332,490 S | 1/1993 | Brown et al. | |
| 5,196,025 A | 3/1993 | Ranalletta et al. | |
| 5,231,993 A | 8/1993 | Harber et al. | |
| 5,267,963 A | 12/1993 | Bachynsky | |
| 5,269,799 A * | 12/1993 | Daniel | 606/182 |
| 5,279,294 A | 1/1994 | Anderson et al. | 128/633 |
| 5,304,193 A | 4/1994 | Zhadanov | |
| 5,318,583 A * | 6/1994 | Rabenau et al. | 606/182 |
| 5,318,584 A * | 6/1994 | Lange et al. | 606/182 |
| 5,320,607 A | 6/1994 | Ishibashi | |
| 5,324,303 A | 6/1994 | Strong et al. | 606/181 |
| 5,350,392 A | 9/1994 | Purcell et al. | |
| 5,527,334 A | 6/1996 | Kanner et al. | |
| 5,575,777 A | 11/1996 | Cover et al. | |
| 5,628,764 A | 5/1997 | Schraga | |
| D393,716 S | 4/1998 | Brenneman et al. | |
| D393,717 S | 4/1998 | Brenneman et al. | |
| 5,741,288 A | 4/1998 | Rife | |
| 5,797,942 A | 8/1998 | Schraga | |
| 5,868,772 A | 2/1999 | LeVaughn et al. | |
| 5,916,230 A | 6/1999 | Brenneman et al. | |
| 5,951,492 A | 9/1999 | Douglas et al. | |
| 5,951,493 A | 9/1999 | Douglas et al. | |
| 5,954,738 A | 9/1999 | LeVaughn et al. | |
| 5,984,940 A * | 11/1999 | Davis et al. | 606/181 |
| 6,022,366 A | 2/2000 | Schraga | |
| 6,045,567 A | 4/2000 | Taylor et al. | |
| 6,048,352 A | 4/2000 | Douglas et al. | |
| 6,050,977 A | 4/2000 | Adams et al. | |
| 6,090,078 A | 7/2000 | Erskine et al. | |
| 6,090,124 A | 7/2000 | Weekes | 606/182 |
| 6,093,156 A | 7/2000 | Cunningham et al. | |
| 6,099,484 A | 8/2000 | Douglas et al. | |
| 6,152,942 A | 11/2000 | Brenneman et al. | |
| 6,156,051 A | 12/2000 | Schraga et al. | |
| 6,168,606 B1 | 1/2001 | Levin et al. | |
| 6,197,040 B1 | 3/2001 | LeVaughn et al. | 606/182 |
| 6,210,421 B1 | 4/2001 | Bocker | |
| 6,231,531 B1 | 5/2001 | Lum et al. | |
| 6,283,982 B1 | 9/2001 | LeVaughn et al. | 606/172 |
| 6,306,152 B1 | 10/2001 | Verdonk et al. | |
| 6,322,574 B1 | 11/2001 | Lloyd et al. | |
| 6,364,889 B1 | 4/2002 | Kheiri et al. | |
| 6,379,317 B1 | 4/2002 | Kintzing et al. | 600/573 |
| 6,409,740 B1 | 6/2002 | Kuhr et al. | |
| 6,419,661 B1 | 7/2002 | Kuhr et al. | |
| 6,432,120 B1 | 8/2002 | Teo | |
| 6,451,040 B1 | 9/2002 | Purcell | |
| 6,514,270 B1 | 2/2003 | Schraga | |
| 6,537,292 B1 | 3/2003 | Lee | |
| 6,561,989 B2 | 5/2003 | Whitson et al. | |
| 6,602,268 B2 | 8/2003 | Kuhr et al. | 606/181 |
| 6,607,543 B2 | 8/2003 | Purcell et al. | |
| 6,749,618 B2 | 6/2004 | LeVaughn et al. | |
| 6,752,817 B2 | 6/2004 | Flora et al. | |
| 6,837,858 B2 | 1/2005 | Cunningham et al. | |
| 7,087,068 B1 * | 8/2006 | Marshall et al. | 606/182 |
| 7,144,404 B2 | 12/2006 | Whitson | |
| 7,238,192 B2 | 7/2007 | List et al. | |
| 7,303,573 B2 | 12/2007 | D'Agostino | |
| 2002/0022789 A1 | 2/2002 | Perez et al. | |
| 2002/0087180 A1 | 7/2002 | Searle et al. | 606/181 |
| 2003/0171699 A1 | 9/2003 | Brenneman | |
| 2003/0187470 A1 | 10/2003 | Chelak et al. | |
| 2003/0216767 A1 | 11/2003 | List et al. | |
| 2004/0059256 A1 | 3/2004 | Perez | |
| 2004/0248312 A1 | 12/2004 | Vreeke et al. | |
| 2005/0085840 A1 | 4/2005 | Yi et al. | |
| 2005/0090850 A1 | 4/2005 | Thoes et al. | |
| 2005/0149090 A1 * | 7/2005 | Morita et al. | 606/181 |
| 2006/0247670 A1 | 11/2006 | LeVaughn et al. | |
| 2008/0140105 A1 | 6/2008 | Zhong et al. | |
| 2008/0167673 A1 | 7/2008 | Zhong et al. | |
| 2008/0195133 A1 | 8/2008 | Zhong et al. | |
| 2010/0179579 A1 | 7/2010 | Purcell | |

FOREIGN PATENT DOCUMENTS

| | | |
|---|---|---|
| EP | 0 204 892 A2 | 12/1986 |
| EP | 0 569 124 A1 | 11/1993 |
| EP | 0 894 471 A2 | 2/1999 |
| EP | 0 898 936 A2 | 3/1999 |
| EP | 0 958 783 A1 | 11/1999 |
| EP | 1 535 573 A2 | 6/2005 |
| EP | 1 541 088 A1 | 6/2005 |
| JP | 2000175889 | 6/2000 |
| WO | WO 02/100278 A1 | 12/2002 |
| WO | WO 2004/103178 A1 | 12/2004 |
| WO | WO 2005/001418 | 1/2005 |
| WO | WO 2005/046477 A2 | 5/2005 |
| WO | WO 2005/077275 A1 | 8/2005 |
| WO | WO 2006/031535 A2 | 4/2006 |
| WO | WO 2006/096540 A1 | 9/2006 |
| WO | WO 2006/096630 A1 | 9/2006 |
| WO | WO 2006/107914 A2 | 10/2006 |

OTHER PUBLICATIONS

International Search Report corresponding to co-pending International Patent Application No. PCT/US2006/007899, European Patent Office, dated Jul. 31, 2006, 3 pages.

* cited by examiner

LANCET RELEASE MECHANISM

CROSS-REFERENCE TO RELATED APPLICATIONS

This application is a U.S. national stage of International Application No. PCT/US2006/007899, filed Mar. 3, 2006, which claims priority to Application No. 60/658,650, filed on Mar. 4, 2005, which is incorporated by reference in its entirety.

FIELD OF THE INVENTION

The present invention relates generally to diagnostic instruments and, more particularly, to a lancet-release mechanism for a lancing device.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, determining glucose in body fluids is important to diabetic individuals who must frequently check their blood glucose levels to regulate the glucose intake in their diets.

One method of obtaining a body fluid sample, such as a whole blood sample, is to use a lancing device. The whole blood sample may then be used to determine the glucose concentration of an individual. Existing lancing devices use a lancet to pierce the tissue of the skin, allowing a blood sample to form on the skin's surface. Typically, lancing devices hold the lancet within them when the lancet is not in use, so as to shield the user from injury as well as to assist in preventing or inhibiting contamination.

Existing lancing devices require two-handed operation, are dangerous, or are ineffective in releasing the lancet. Two-handed operation requires that one hand hold the lancing device while the other hand removes the lancet. This is inconvenient to many users as the lancet is small, and may cause safety problems as the lancet could pierce the user's skin inadvertently. This can cause the user pain and may also transmit diseases. Some one-handed designs eject the lancet too hard such that ejecting the lancet becomes dangerous if the lancet is not re-shielded. Still other one-handed designs do not eject the lancet effectively, as the lancet is not released from the lancet holder even after the user depresses the release mechanism. Yet other one-handed designs have complicated release mechanisms internally, such that if a user drops the lancing device, the release mechanism may jam and no longer eject the lancet from the lancing device.

It would be desirable to have a lancing device and a method for using a lancing device that addresses these issues.

SUMMARY OF THE INVENTION

According to one embodiment of the present invention, a lancing device is disclosed. The lancing device comprises a lancet holder and a lancet-release mechanism. The lancet holder includes an aperture being adapted to receive a lancet assembly therein. The lancet holder is adapted to move the lancet assembly between a resting position, a cocking position, and a puncture position. The lancet-release mechanism includes (i) a release button located adjacent to and external from the lancing device, and (ii) a beam attached to the release button. The beam extends into the lancing device and the lancet holder. The beam is adapted to engage the lancet assembly. The release button and attached beam are adapted to eject the lancet assembly from the lancet holder.

According to another embodiment of the present invention, a lancing device is disclosed. The lancing device includes the above-described features. The lancet-release mechanism of the above-described device further includes a spring located adjacent to and engaging the beam. The spring is adapted to bias the beam to engage the lancet assembly once it is received by the lancet holder. The release button and the attached beam, along with the spring, are adapted to eject the lancet assembly from the lancet holder.

According to yet another embodiment of the present invention, a method for ejecting a lancet assembly from a lancet holder is disclosed. The method comprises the acts of providing the above-described lancing device and lancet-release mechanism and moving the lancet-release mechanism in the direction of the lancet assembly to eject the lancet assembly from the lancet holder of the lancing device.

The above summary of the present invention is not intended to represent each embodiment, or every aspect, of the present invention. Additional features and benefits of the present invention are apparent from the detailed description and figures set forth below.

BRIEF DESCRIPTION OF THE DRAWINGS

FIG. 1b is a bottom view of the lancing device of FIG. 1a.

DESCRIPTION OF ILLUSTRATED EMBODIMENTS

The present invention is directed to a lancet-release mechanism for incorporation into a stand-alone lancing device or into a lancing device that is incorporated into a meter or similar testing device. The lancing device is adapted to receive a lancet for use in drawing a body fluid from a test subject. The body fluid generally contains at least one analyte that may then be examined to determine its concentration in the body fluid sample.

Lancing devices and lancets may be used to produce a blood or body fluid sample from a test subject. This sample may then be analyzed with a meter and test strip, or similar devices, to determine the concentration of the analyte to be examined. Examples of the types of analytes that may be collected with a lancing device include glucose, lipid profiles (e.g., cholesterol, triglycerides, LDL and HDL), microalbumin, hemoglobin A1C, fructose, lactate, or bilirubin.

Figure 1A:
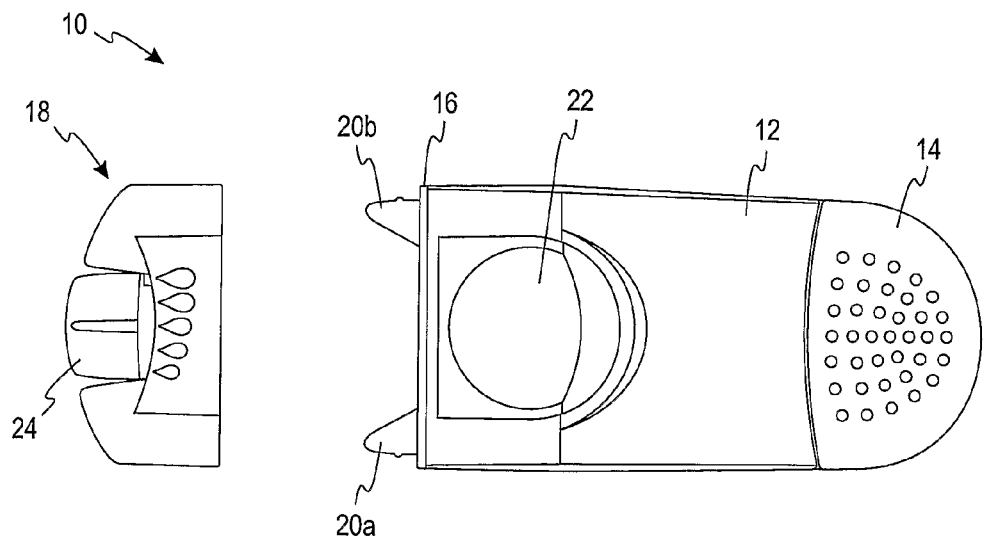
FIG. 1a is a top view of a lancing device, according to one embodiment of the present invention.
Figure 1B:
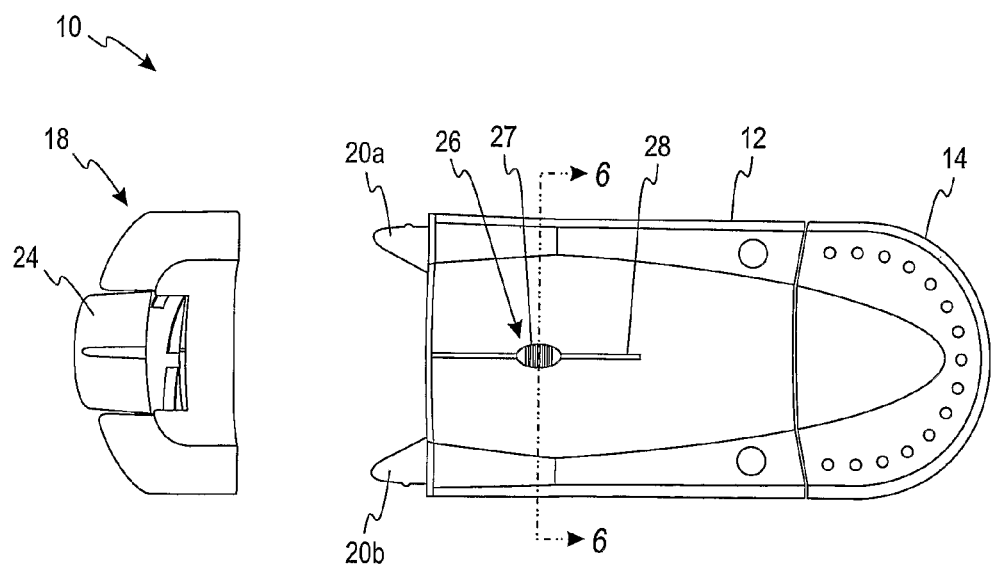
Figure 2:
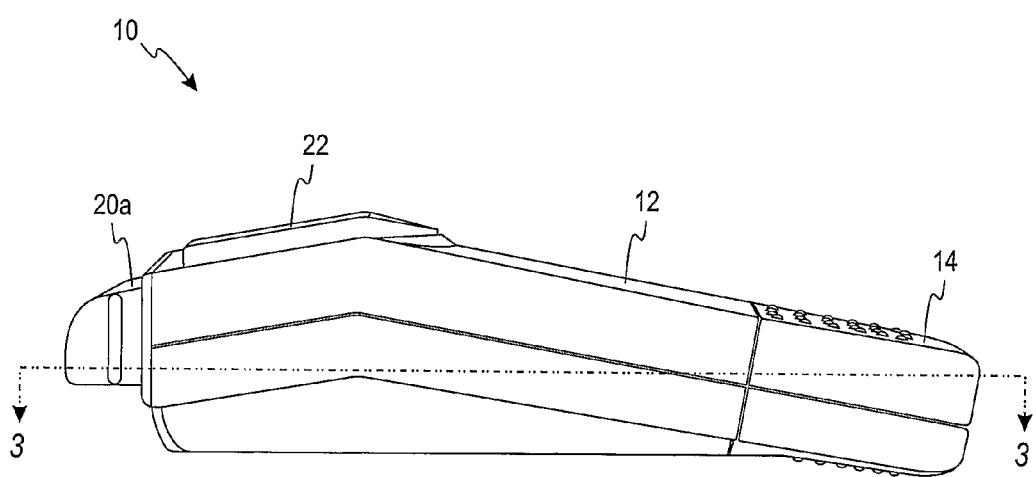
FIG. 2 is a side view of the lancing device of FIGS. 1a-b.

Turning now to the drawings and initially to FIGS. 1-2, a lancing device 10 for obtaining a fluid sample from a test subject is illustrated, according to one embodiment of the present invention. The lancing device 10 has a main housing 12 and a movable housing 14 that is movable relative to the main housing 12. An endcap support 16 is connected to the main housing 12 on the testing end of the lancing device 10. An endcap 18 may be removably attached to the endcap support 16. When attached, the endcap 18 is retained on the endcap support 16 by a pair of support arms 20a-b integrally formed with the endcap support 16.

Figure 5:
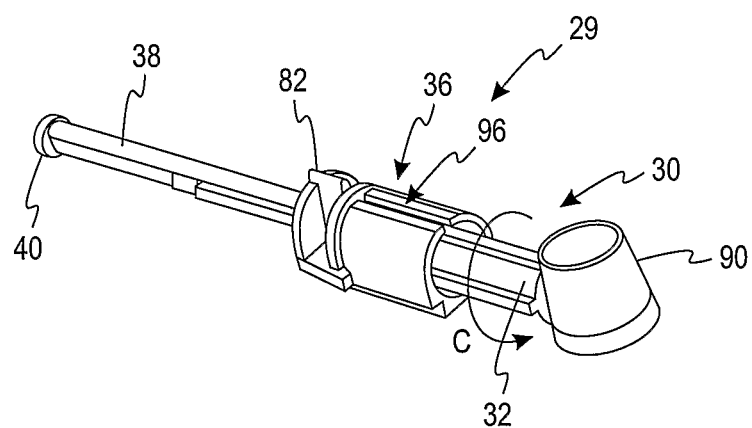
FIG. 5 is a perspective view of a lancing mechanism, according to one embodiment of the present invention.

To use the lancing device 10, the movable housing 14 is pulled away from the main housing 12 to move an internal lancing mechanism 29 (as best illustrated in FIG. 5) to a cocked position, and then a pushbutton 22 is pushed to actuate the lancing mechanism 29 so that the sharp tip of a lancet is forced through an aperture (not shown) in the endcap 18. The lancing device 10 may be provided with a number of different endcaps 18, each having a different width, to facilitate the formation of skin punctures of various depths. Alternatively, the endcap 18 may include an adjustable dial 24 for allowing punctures of different depths to be performed utilizing a single endcap 18.

The lancing device 10 includes a lancet-release mechanism 26 having a release button 27 accessible external to the lancing device 10. The release button 27 may include a depression (illustrated in FIGS. 7-8) or tactile features (illustrated in FIGS. 2 and 6) to more easily allow a user to engage the release button 27. The lancet-release mechanism 26 includes a beam 56 (illustrated in FIG. 6) that is attached to the release button 27 and extends therefrom into the main housing 12 of the lancing device 10. The beam 56 extends into the main housing 12 through an aperture 28 formed in the main housing 12. The lancet-release mechanism 26 also includes a tab 57 (FIG. 6) extending from the beam 56 opposite the release button 27.

Figure 3:
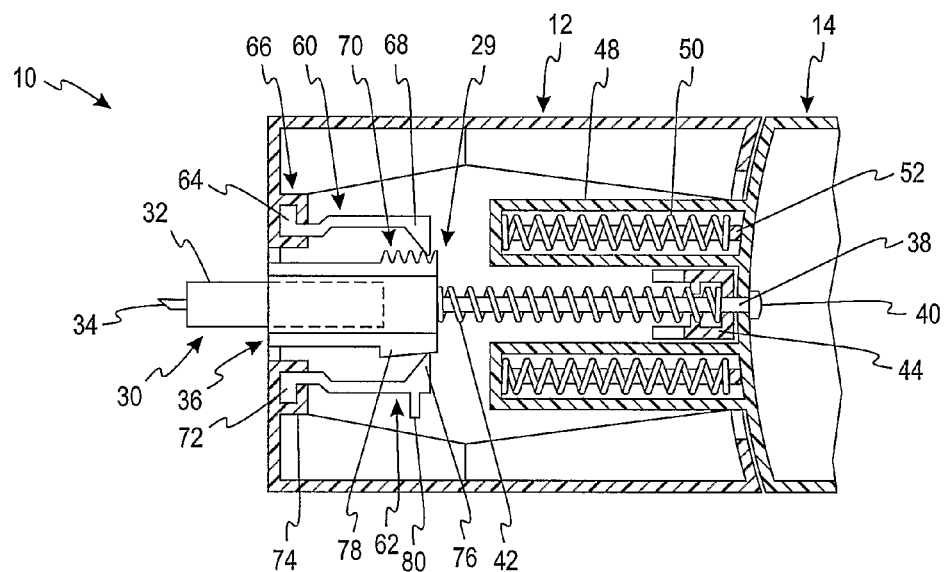
FIG. 3 is a cross-sectional, top view of the lancing device of FIG. 2 in a resting position.

Turning now to FIG. 3, a cross-sectional view of a portion of the lancing device 10 is illustrated with the endcap 18 and endcap support 16 not shown. A lancet assembly 30 having a lancet body 32 and a lance 34 is received within an internal cylindrical aperture 58 (FIG. 6) formed in a generally cup-shaped lancet holder 36. The lancet holder 36 is connected to an elongated shaft 38 by being integrally formed therewith. The shaft 38 has an enlarged end 40 that is supported within the movable housing 14. A drive spring 42 is disposed around the shaft 38 between the lancet holder 36 and a spring stop 44 (see also FIG. 4) integrally formed with the main housing 12.

The movable housing 14 has a pair of elongate spring trays 48 integrally formed therewith. A return spring 50 is disposed within each of the spring trays 48, a first end of each return spring 50 being disposed against an internal surface of the spring tray 48 and a second end of each return spring 50 being disposed against a spring stop 52 integrally formed with the main housing 12. The spring stops 52 extend into the spring trays 48 through an elongate slot 54 (see FIG. 4) formed in the bottom portion of each tray 48.

A damping arm 60 and a retaining arm 62 are disposed adjacent opposite sides of the lancet holder 36. The damping arm 60 has a first end 64 that is held within a retaining structure 66 integrally formed with the main housing 12. A second pointed end 68 of the damping arm 60 is disposed adjacent a corrugated surface 70 formed on an outside portion of the lancet holder 36. The retaining arm 62 has a first end 72 that is held within a retaining structure 74 integrally formed with the main housing 12. A second pointed end 76 of the retaining aim 62 is disposed adjacent an angled stop member 78. The lower side of the retaining arm 62 rests on a support member 80. The arms 60, 62 are biased inwardly towards the lancet holder 36 so that they make contact with the respective outer sides of the lancet holder 36.

Figure 4:
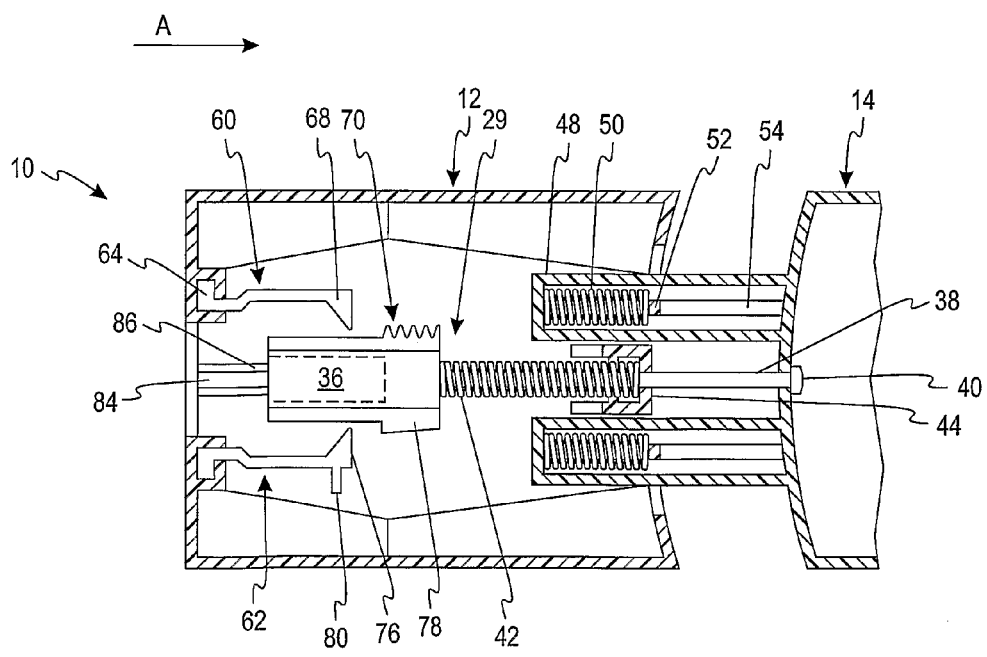
FIG. 4 is a cross-sectional, top view of the lancing device of FIG. 2 in a cocking position.

FIG. 3 illustrates the interior of the lancing device 10 when the lancing device 10 is not in use. In this position, the lancet holder 36 is disposed in a resting position between a puncture position and a cocked position. FIG. 4 illustrates the interior of the lancing device 10 (the lancet assembly 30 is not shown) when the lancet holder 36 is in a cocked position in which the movable housing 14 has been pulled away from the main housing 12.

Referring to FIG. 4, to move the lancet holder 36 from its resting position to its cocked position, the movable housing 14 is pulled away from the main housing 12 in the direction of Arrow A. The movable housing 14 continues to be pulled—against the force of the drive spring 42—until the angled stop member 78 formed on the lancet holder 36 moves past (to the right of as illustrated in FIG. 4) the pointed end 76 of the retaining arm 62. At that point, the bias of the retaining arm 62 will force its pointed end 76 inwardly, so that the pointed end 76 makes contact with the side of the lancet holder 36 disposed on the testing end side of the angled stop member 78. When in that cocked position, movement of the lancet holder 36 in the direction of Arrow B due to the drive spring 42 is prevented because of the contact between the pointed end 76 of the retaining aim 62 and the angled stop member 78. After the lancet holder 36 is placed in the cocked position, the user allows the return springs 50 to force the movable housing 14 back to its initial position adjacent the main housing 12.

The lancet holder 36 is guided between its resting and cocked positions by a guide rib 82 (FIG. 5) formed on the bottom portion of the lancet holder 36 that rides within a groove 84 formed between a pair of raised guide rails 86 formed in a bottom interior portion of the main housing 12. As the lancet holder 36 is moved from the resting position to the cocked position, the release button 27 slides within the aperture 28 (FIG. 1b) as the lancet assembly 30 received within the lancet holder 36 engages the beam 56 (FIG. 6) of the free-floating lancet-release mechanism 26.

To perform a puncture on a test subject's skin, the endcap 18 is attached to the lancing device 10. The lancet holder 36 may be in the cocked position at the time the endcap 18 is attached or may be cocked once the endcap 18 is in position. The endcap 18 is then placed firmly against the skin where the puncture is to be made, and the pushbutton 22 is depressed. Depressing the pushbutton 22 causes an angled release arm (not shown), integrally formed with the bottom of the pushbutton 22 and which passes through an aperture (not shown) in the main housing 12, to force the retaining arm 62 away from the lancet holder 36. Thus, the lancet holder 36 is no longer prevented from moving in the direction of Arrow B by the contact of the angled stop member 78 with the pointed end 76 of the retaining arm 62. A spring mechanism—for example, an elastically deformable foam material—may be disposed between the pushbutton 22 and a portion of the main housing 12 to bias the pushbutton 22 to its non-actuated position.

Upon release of the lancet holder 36 as described above, the drive spring 42 will force the lancet holder 36 in the direction of Arrow B until the sharp point of the lance 34 (FIG. 3) passes through the aperture (not shown) in the endcap 18 to make the puncture. When the puncture is made, the drive spring 42 will be in a stretched position, and after the puncture is made the contraction of the drive spring 42 will draw the lancet holder 36 back towards its resting position shown in FIG. 3.

As the lancet holder 36 moves from its puncture position back to its resting position shown in FIG. 3, the pointed tip 68 of the damping arm 60 will make frictional contact with the corrugated surface 70. This frictional contact decelerates or dampens the movement of the lancet holder 36. Such damping assists in preventing or inhibiting the drive spring 42—and its natural tendency to oscillate (due to its being elastically deformable)—from causing a second, unintended skin puncture to be made. As used herein, the term "corrugated" refers to a surface having raised ribs or other structures, either regularly or irregularly spaced, for providing an increased amount of friction when the surface is brought into contact with a damping member.

Turning now to FIG. 5, a perspective view of the lancing mechanism 29 is illustrated, according to one embodiment of the present invention. The lancet mechanism 29 includes the lancet holder 36 adapted to receive the lancet assembly 30. The lancet holder 36 is provided with a slot 96 through which the beam 56 (FIG. 6) of the lancet-release mechanism 26 can extend. The slot 96 is adapted to allow the beam 56 to slide therein. As illustrated in FIG. 5, the lancet assembly 30 is disposed within the generally cylindrical aperture formed in the lancet holder 36. The lancet assembly 30 is shown with a protective cap 90 that has a portion that is integrally formed with the lancet body 32 and which covers the sharp point of the lance 34. Prior to using the lancing device 10, the lancet body 32 of a new lancet assembly 30 is inserted into the cylindrical aperture disposed in the lancet holder 36, and then the protective cap 90 is twisted off of the lancet assembly 30, in the direction of the Arrow C shown in FIG. 5.

Figure 6:
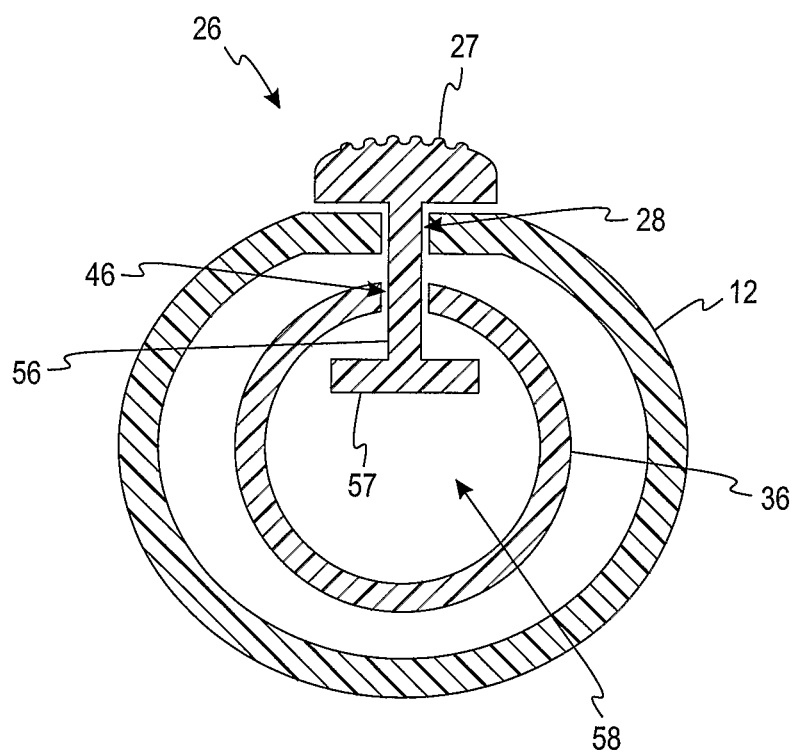
FIG. 6 is a cross-sectional view of the lancing device of FIG. 1b, according to one embodiment of the present invention.

Referring also to FIG. 6, a cross-sectional view of the lancet-release mechanism 26 is illustrated with respect to the lancet holder 36 and the main housing 12. The lancet-release mechanism 26 includes the release button 27 attached to the beam 56 that extends therefrom. The beam 56 extends into the lancing device 10 and the central aperture 58 of the lancet holder 36 through the aperture 28 formed in the main housing 12 and the slot 96 formed in the lancet holder 36, respectively. A tab 57 extends from the beam 56 opposite the release button 27. The tab 57 extends perpendicular to the beam 56 and is adapted to additionally engage the lancet assembly 30. The tab 57 also assists in maintaining the lancet-release mechanism 26 in the proper orientation such that the beam 56 does not exit the aperture 28 or slot 96.

According to one embodiment of the present invention, the release button 26, beam 56, and tab 57 are a single, integrally formed component. During manufacture, the beam 56 is inserted into the slot 96 of the lancet holder 36 and aperture 28 formed in the main housing 12. As illustrated in FIG. 2, the slot 96 extends to the testing end of the main housing 12 to allow the beam 56 to be inserted therein. Once the beam 56 is inserted into the aperture 28 and lancet holder 36, the endcap support 16 is attached to the main housing 12 and the lancet-release mechanism 26 is secured into position. Alternatively, in other embodiments of the present invention, the release button 27 and/or the tab 57 may be attached to the beam 56 after the beam 56 is extended through the aperture 28 and the lancet holder 36.

Figure 7A:
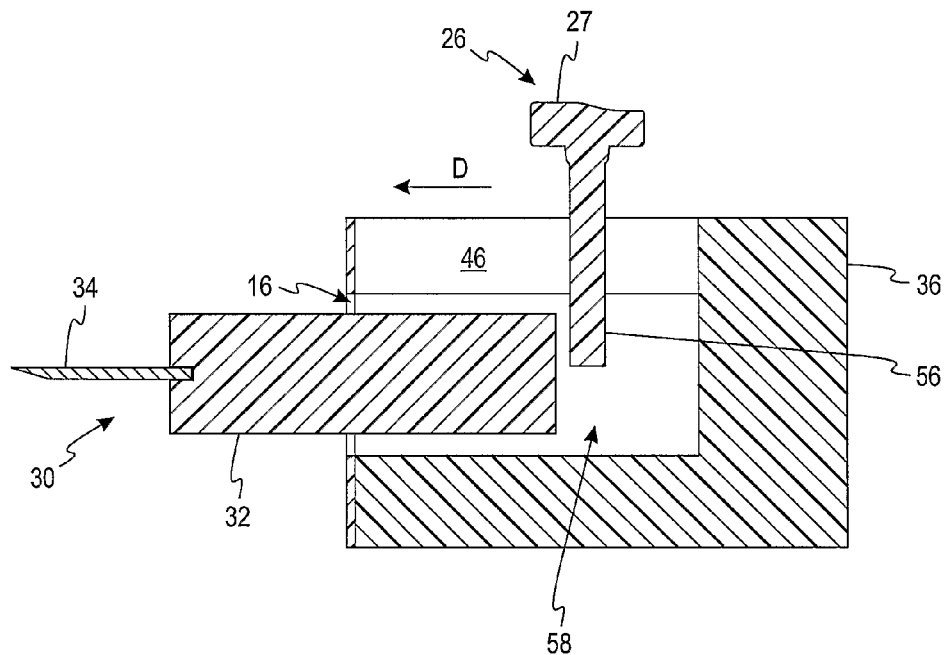
FIG. 7a is a cross-sectional view of a lancet-release mechanism, lancet holder, and lancet assembly with the lancet-release mechanism in a resting position, according to one embodiment of the present invention.
Figure 7B:
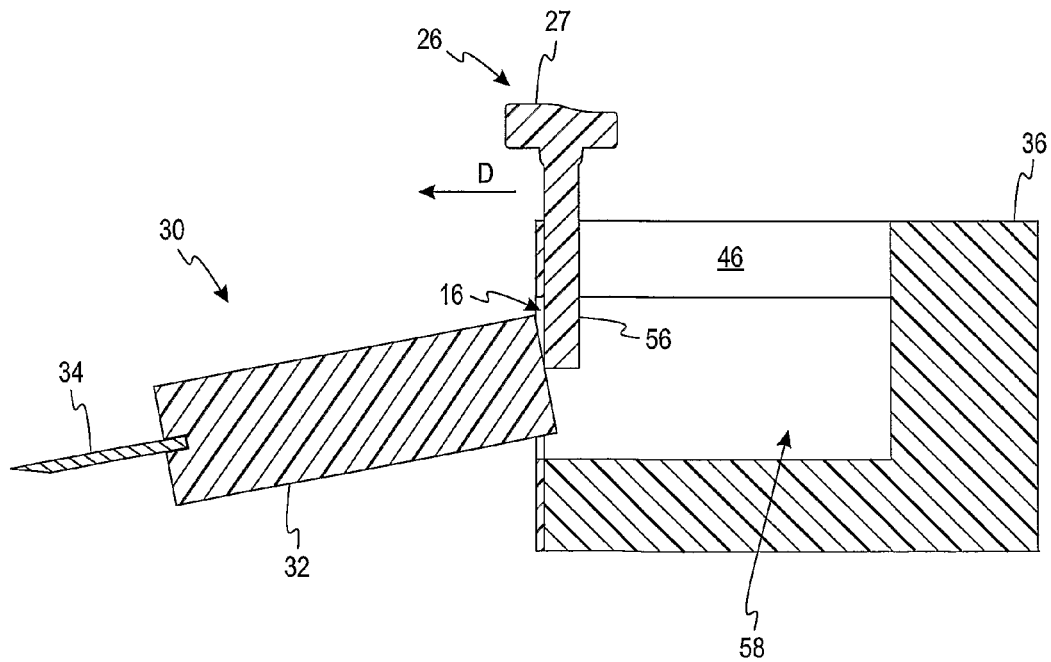
FIG. 7b is a cross-sectional view of the lancet-release mechanism, lancet holder, and lancet assembly of FIG. 7a with the lancet-release mechanism in a release position.

Referring also to FIGS. 7a-7b, the beam 56 of the lancet-release mechanism 26 extends into the central aperture 58 of the lancet holder 36 behind the lancet body 32 of the lancet assembly 30, opposite the lance 34. In this position, the lancet-release mechanism 26 can be utilized by a user to eject the lancet assembly 30 from the lancet holder 36. To eject the lancet assembly 30, the user engages the release button 27 and moves the lancet-release mechanism 26 in the direction of the lance 34, illustrated by Arrow D in the FIGS. 7a-b. As the lancet-release mechanism 26 is moved by the user, the beam 56 and tab 57 (FIG. 6) engage the lancet body 32. Further movement of the lancet-release mechanism 26 causes the beam 56 and tab 57 to begin to eject the lancet assembly 30 from the central aperture 58 of the lancet holder 36. As the lancet-release mechanism 26 is being moved substantially toward the end of the lancet holder 36, the lancet assembly 30 is ejected from the lancet holder 36.

Figure 8A:
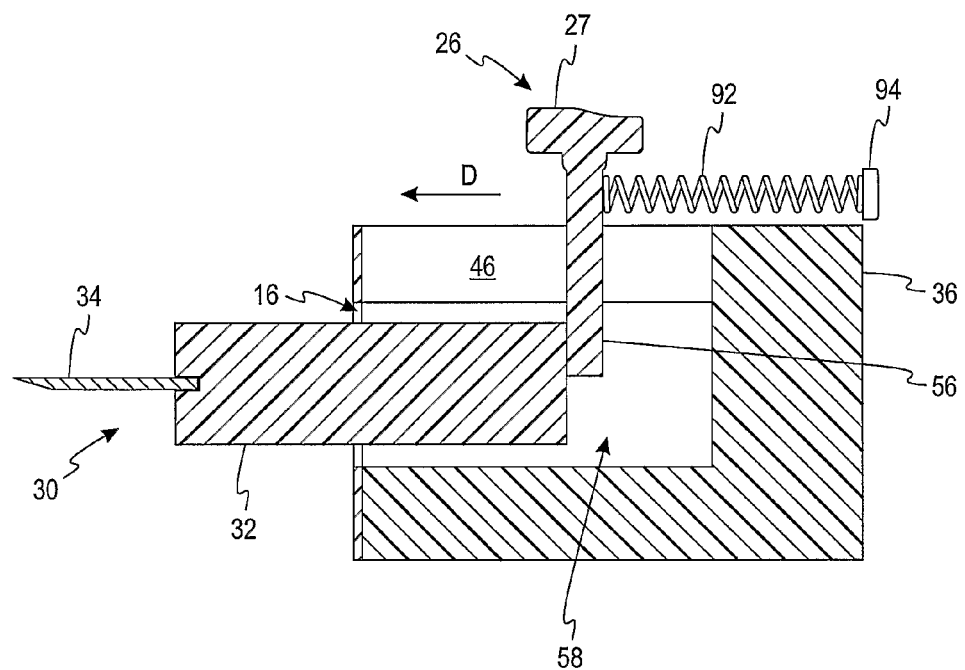
FIG. 8a is a cross-sectional view of a lancet-release mechanism, lancet holder, lancet assembly, and spring with the lancet-release mechanism in a resting position, according to another embodiment of the present invention.
Figure 8B:
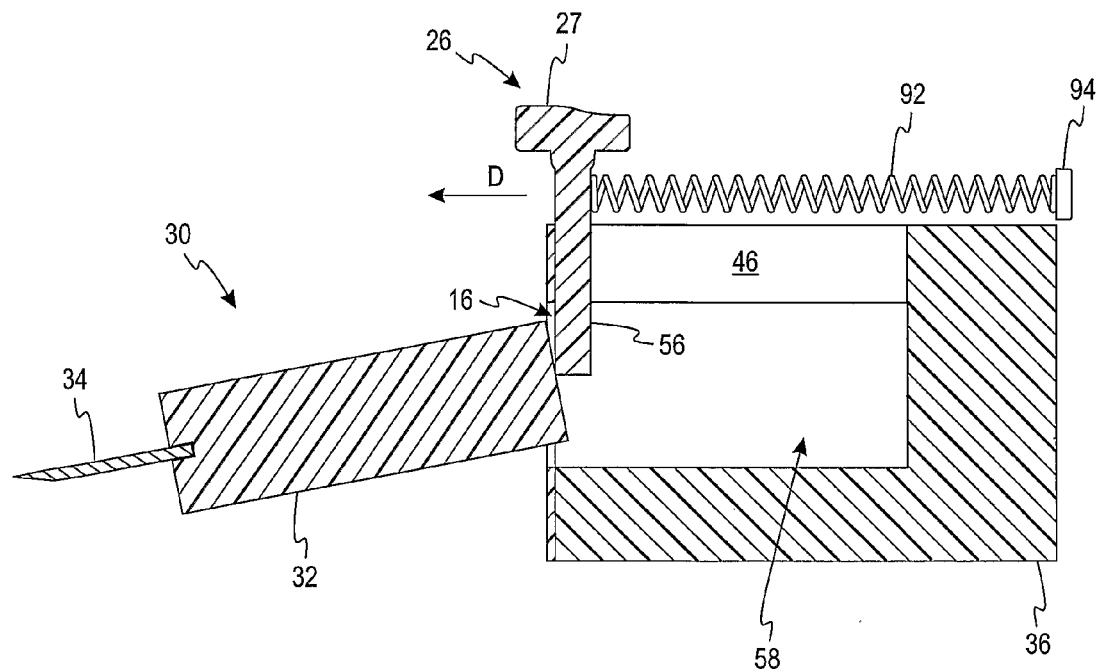
FIG. 8b is a cross-sectional view of a lancet-release mechanism, lancet holder, lancet assembly, and spring of FIG. 8a with the lancet-release mechanism in a release position.

Referring now to FIGS. 8a-8b, the lancet-release mechanism 26, lancet assembly 30, and lancet holder 36 are illustrated according to another embodiment of the present invention. In the illustrated embodiment, a spring 92 and a spring stop 94 are provided within a main housing of a lancing device. The spring 92 is located between the beam 56 of the lancet-release mechanism 26 and the spring stop 94. The spring 92 is adapted to engage the beam 56 of the lancet-release mechanism 26, and bias the lancet-release mechanism 26 in the direction of Arrow D, adjacent the lancet assembly 30. As the lancet assembly 30 is received within the central aperture 58 of the lancet holder 36, the lancet body 32 forces the beam 56, and thus the lancet-release mechanism 26, opposite Arrow D, forcing the spring 92 to contract. By utilizing a spring 92 and spring stop 94 as illustrated, the beam 56 and tab 57 (FIG. 6) are kept in constant contact with the lancet body 32 and the force required from a user to eject the lancet assembly 30 from the lancet holder 36 is reduced.

ALTERNATIVE EMBODIMENT A

A lancing device comprising:

a lancet holder forming an aperture, the aperture being adapted to receive a lancet assembly therein, the lancet holder being adapted to move the lancet assembly between a resting position, a cocking position, and a puncture position; and a lancet-release mechanism including (i) a release button located adjacent to and external from the lancing device, and (ii) a beam attached to the release button, the beam extending into the lancing device and the lancet holder, the beam being adapted to engage the lancet assembly, wherein the release button and attached beam are adapted to eject the lancet assembly from the lancet holder.

ALTERNATIVE EMBODIMENT B

The lancing device of Alternative Embodiment A further comprising an aperture formed in the lancing device, wherein the beam of the lancet-release mechanism extends into the lancing device through the aperture, the aperture allowing the beam to move as the lancet assembly is moved between the resting position, the cocking position, and the puncture position.

ALTERNATIVE EMBODIMENT C

The lancing device of Alternative Embodiment A wherein the release button of the lancet-release mechanism includes a depression that assists a user in engaging the release button.

ALTERNATIVE EMBODIMENT D

The lancing device of Alternative Embodiment A, wherein the release button of the lancet-release mechanism includes tactile features that assist a user in engaging the release button.

ALTERNATIVE EMBODIMENT E

The lancing device of Alternative Embodiment A, wherein the lancet-release mechanism further includes a tab extending from the beam opposite the release button, the tab extending perpendicular to the beam, the tab being adapted to engage the lancet assembly.

ALTERNATIVE EMBODIMENT F

A lancing device comprising:
a lancet holder having an aperture, the aperture being adapted to receive a lancet assembly therein, the lancet holder being adapted to move the lancet assembly between a resting position, a cocking position, and a puncture position; and
a lancet-release mechanism including
(i) a release button located adjacent to and external from the lancing device,
(ii) a beam attached to the release button, the beam extending into the lancing device and the lancet holder, the beam being adapted to engage the lancet assembly, and
(iii) a spring located adjacent to and engaging the beam, the spring being adapted to bias the beam to engage the lancet assembly once it is received by the lancet holder,
wherein the release button and the attached beam, along with the spring, are adapted to eject the lancet assembly from the lancet holder.

ALTERNATIVE EMBODIMENT G

The lancing device of Alternative Embodiment F further comprising an aperture formed in the lancing device, wherein the beam of the lancet-release mechanism extends into the lancing device through the aperture, the aperture allowing the beam to move as the lancet assembly is moved between the resting position, the cocking position, and the puncture position.

ALTERNATIVE EMBODIMENT H

The lancing device of Alternative Embodiment F, wherein the spring is located between the lancet holder and a main housing of the lancing device.

ALTERNATIVE EMBODIMENT I

The lancing device of Alternative Embodiment F, wherein the lancet-release mechanism further includes a tab extending from the beam opposite the release button, the tab extending perpendicular to the beam, the tab being adapted to engage the lancet assembly.

ALTERNATIVE PROCESS J

A method for ejecting a lancet assembly from a lancet holder, the method comprising the acts of:
providing a lancing device that includes the lancet holder having an aperture, the aperture being adapted to receive the lancet assembly therein, the lancing device being adapted to move the lancet assembly between a resting position, a cocking position, and a puncture position;
providing a lancet-release mechanism including
(i) a release button located adjacent to and external from the lancing device, and
(ii) a beam attached to the release button, the beam extending into the lancing device and the lancet holder, the beam being adapted to engage the lancet assembly; and
moving the lancet-release mechanism in the direction of the lancet assembly to eject the lancet assembly from the lancet holder of the lancing device.

ALTERNATIVE PROCESS K

The method of Alternative Process J further comprising the act of providing a spring within the lancing device, the spring being located adjacent to and engaging the beam of the lancet-release mechanism, the spring being adapted to bias the beam to engage the lancet assembly once the lancet assembly is received by the lancet holder.

ALTERNATIVE PROCESS L

The method of Alternative Process J further comprising the act of assisting the movement of the lancet-release mechanism in the direction of the lancet assembly by utilizing the spring.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

The invention claimed is:

1. A lancing device comprising:
a lancet holder having an aperture, the aperture being configured to receive a lancet assembly therein, the lancet holder being configured to move the lancet assembly between a resting position, a cocking position, and a puncture position; and
a lancet-release mechanism including
(i) a release button located adjacent to and external from the lancing device,
(ii) a beam attached to the release button, the beam extending into the lancing device and the lancet holder, the beam being configured to engage the lancet assembly, and
(iii) a spring located adjacent to and engaging the beam, the spring being configured to contract as the lancet assembly is received by the lancet holder,
wherein the release button and the attached beam, along with the spring, are positioned to eject the lancet assembly from the lancet holder by biasing the beam against the lancet assembly, the biasing at least partially due to the spring expanding from a compressed state.

2. The lancing device of claim 1, further comprising an aperture formed in the lancing device, wherein the beam of the lancet-release mechanism extends into the lancing device through the aperture, the aperture allowing the beam to move as the lancet assembly is moved between the resting position, the cocking position, and the puncture position.

3. The lancing device of claim 1, wherein the spring is located between the lancet holder and a main housing of the lancing device.

4. The lancing device of claim 1, wherein the lancet-release mechanism further includes a tab extending from the beam opposite the release button, the tab extending perpendicular to the beam, the tab being configured to engage the lancet assembly.

5. The lancing device of claim 1, wherein the lancet holder includes an exterior shell that forms the aperture.

6. The lancing device of claim 1, wherein the release button of the lancet-release mechanism includes a depression that assists a user in engaging the release button.

7. The lancing device of claim 1, wherein the release button of the lancet-release mechanism includes tactile features that assist a user in engaging the release button.

8. The lancing device of claim 1, wherein the spring is configured to move in the same direction as the lancet assembly.

9. A method for ejecting a lancet assembly from a lancet holder, the method comprising the acts of:
providing a lancing device that includes a lancet holder having an aperture, the aperture being configured to receive a lancet assembly therein, the lancing device being configured to move the lancet assembly between a resting position, a cocking position, and a puncture position;
providing a lancet-release mechanism including
(i) a release button located adjacent to and external from the lancing device, and
(ii) a beam attached to the release button, the beam extending into the lancing device and the lancet holder, the beam being configured to engage the lancet assembly; and
providing a spring within the lancing device, the spring being configured to expand from a compressed state to assist moving the lancet-release mechanism in a similar general direction of movement as the lancet assembly thereby causing the lancet assembly to be ejected from the lancet holder of the lancing device and thereby reducing a force needed to be applied to the beam to cause the lancet assembly to be ejected from the lancet holder.

10. The method of claim 9, further comprising the act of forming an aperture in the lancing device such that the beam of the lancet-release mechanism extends into the lancing device through the aperture, the aperture being configured to allow the beam to move as the lancet assembly is moved between the resting position, the cocking position, and the puncture position.

11. The method of claim 9, wherein the spring is located between the lancet holder and a main housing of the lancing device.

12. The method of claim 9, wherein the spring is located adjacent to and engaging the beam, and further wherein the release button and the attached beam, along with the spring, are configured to eject the lancet assembly from the lancet holder.

13. A lancing device comprising:
a lancet holder forming an aperture, the aperture configured to receive a lancet assembly therein, the lancet holder configured to move the lancet assembly between a resting position, a cocking position, and a puncture position;
a lancet-release mechanism including
(i) a release button located adjacent to and external from the lancing device, and
(ii) a beam attached to the release button, the beam extending into the lancet holder, the beam configured to engage the lancet assembly; and
a spring located adjacent to and engaging the beam, the spring configured to expand from an initially compressed state to bias the lancet-release mechanism in a similar general direction of movement as the lancet assembly such that the beam of the lancet-release mechanism and the lancet assembly are in constant contact, thereby reducing a force needed to be applied to the beam to cause the lancet assembly to be ejected from the lancet holder.

14. The lancing device of claim 13, wherein the release button of the lancet-release mechanism includes a depression for assisting a use to engage the release button.

15. The lancing device of claim 13, wherein the release button of the lancet-release mechanism includes tactile features for assisting a user to engage the release button.

16. The lancing device of claim 13, further comprising an aperture formed in the lancing device, wherein the beam of the lancet-release mechanism extends into the lancing device through the aperture, the aperture allowing the beam to move as the lancet assembly is moved between the resting position, the cocking position, and the puncture position.

17. The lancing device of claim 13, wherein the spring is located between the lancet holder and a main housing of the lancing device.

18. The lancing device of claim 13, wherein the lancet-release mechanism further includes a tab extending from the beam opposite the release button, the tab extending perpendicular to the beam, the tab configured to engage the lancet assembly.

19. The lancing device of claim 13, wherein the spring is configured to move along a first axis that is generally parallel to a second axis located within the aperture, the lancet assembly configured to be movable along the second axis.

* * * * *

UNITED STATES PATENT AND TRADEMARK OFFICE
CERTIFICATE OF CORRECTION

PATENT NO. : 9,055,898 B2
APPLICATION NO. : 11/885521
DATED : June 16, 2015
INVENTOR(S) : Zhong et al.

Page 1 of 1

It is certified that error appears in the above-identified patent and that said Letters Patent is hereby corrected as shown below:

IN THE SPECIFICATION

Column 4, Line 7, delete "aim" and insert -- arm --, therefor.

Column 4, Line 34, delete "aim" and insert -- arm --, therefor.

Column 5, Line 52, delete "button 26," and insert -- button 27, --, therefor.

Signed and Sealed this
Ninth Day of February, 2016

Michelle K. Lee
*Director of the United States Patent and Trademark Office*